United States Patent [19]

Hobbs

[11] 4,111,218

[45] Sep. 5, 1978

[54] ABSORPTION PROCESS METHOD AND APPARATUS

[75] Inventor: James W. Hobbs, Bartlesville, Okla.

[73] Assignee: Phillips Petroleum Company, Bartlesville, Okla.

[21] Appl. No.: 691,121

[22] Filed: May 28, 1976

Related U.S. Application Data

[62] Division of Ser. No. 474,405, May 30, 1974, Pat. No. 3,967,937.

[51] Int. Cl.² ............................................... F17D 3/01
[52] U.S. Cl. ....................................... 137/2; 137/389; 137/395; 364/118; 364/500; 196/132; 202/160; 203/1; 203/DIG. 18
[58] Field of Search ................ 55/18, 48, 227; 137/14, 137/395, 389, 386, 86; 196/132; 202/160; 203/1, DIG. 18; 235/151.12

[56] References Cited

U.S. PATENT DOCUMENTS

| | | | |
|---|---|---|---|
| 2,476,104 | 7/1949 | Mason | 137/14 |
| 2,976,234 | 3/1961 | Webber | 203/1 |
| 3,050,450 | 8/1962 | Kleiss et al. | 196/132 |
| 3,224,947 | 12/1965 | Lupfer | 196/132 |
| 3,230,154 | 1/1966 | Walker | 196/132 |
| 3,411,308 | 11/1968 | Bellinger | 196/132 |
| 3,446,709 | 5/1969 | Marshall | 55/227 |
| 3,449,215 | 6/1969 | Johnson et al. | 196/132 |

*Primary Examiner*—Martin P. Schwadron
*Assistant Examiner*—G. L. Walton

[57] ABSTRACT

The flow rate of feed material containing a constituent to be absorbed and the flow rate of the absorption medium entering an absorption zone are controlled in response to the content and flow rate of feed material entering the absorption zone and the amount of a desired bottoms constituent in the overhead stream of the absorption zone so that the efficiency of the absorption process is optimized. Under circumstances necessitating maximum production from the absorption zone and its associated stripping zone, the absorption medium flow rate is maintained at a maximum value and the feed flow rate is controlled in response to feed composition and flow as well as the concentration of desired bottom product in the overhead stream. The output of the absorption unit is stabilized by alteration of the flow control apparatus associated with the output stream of the stripping zone in order to alter the amount of control over the output flow. A set point signal which controls the product output flow is generated in response to the predicted rate of delivery of product material to an accumulator and a modified signal related to the liquid level within the accumulator.

6 Claims, 6 Drawing Figures

ABSORPTION PROCESS METHOD AND APPARATUS

This is a division of application Ser. No. 474,405, filed May 30, 1974, now U.S. Pat. No. 3,967,937.

This invention relates to a method and apparatus for operating an absorption process. In another aspect the invention relates to a method and apparatus for optimizing the operation of an absorption zone. In yet another aspect, the invention relates to a method and apparatus for controlling the flow of product from a process. In still another aspect the invention relates to a method of operating an absorption process utilizing two modes of control.

Many processes are known by which the various constituents of a feed material are separated by selective absorption of one or more of the constituents in an absorption medium and subsequent stripping of the absorbed product constituents from the absorption medium. Ordinarily an absorption medium will not selectively absorb all of the desired product constituent contained in the feed material under practical process conditions. While it is possible to decrease the ratio of feed material to absorption medium and achieve increased separation efficiency, this increased efficiency can ordinarily be achieved only by decreasing the rate of production of the process. In the past it has therefore been necessary to compromise between maximum efficiency of separation and maximum production in order to operate an absorption process under conditions which reasonably fulfill both goals. At a time when the efficiency of commercial processes is of increased importance due to a scarcity of many raw materials and increased production costs, and production rate is increasingly important as a result of many product shortages, operation of an absorption process in a manner which permits maximum process efficiency or maximum process output, depending upon process requirements, is desirable.

Another problem associated with selective absorption processes as well as other fluid-producing processes is maintenance of a controlled and preferably uniform product output flow. This is desirable because in many circumstances the output of one process is utilized directly as the input to a subsequent process, and instability in the output of the first process may lead to instability and control problems in the subsequent process. This problem is particularly acute in a situation where the output of the first process must supply both input to a subsequent process and an independently controlled reflux stream to the first process.

It is therefore an object of the invention to provide a method and apparatus for operating an absorption process. A further object of the invention is to provide a method and apparatus for optimizing the operation of an absorption zone. Yet another object is to provide a method and apparatus for controlling the flow of product from a process. Still another object of the invention is to provide a method of operating an absorption process utilizing two modes of control.

In accordance with the invention, a selective absorption process can be operated so that the absorption of a desired product constituent in the feed entering the absorption zone by the absorption medium results in the optimization of the efficiency of the separation performed by the selective absorption or in the maximum production rate of product which can be accommodated by the absorption zone. After the selected absorption of the desired product constituent, the absorbent containing the absorbed product constituent is passed to a stripping zone where the product constituent and absorption medium are separated. The product constituent is withdrawn to an accumulator which supplies recycle product to the stripping zone and also supplies product material to a subsequent process. The supply of the product material to the subsequent process is controlled to avoid unnecessary fluctuations in the output flow of product material from the accumulator by controlling the output product flow in response to the liquid level of the accumulator, the magnitude and direction of the error between actual accumulator liquid level and the desired accumulator liquid level, and the predicted flow of product into the accumulator.

In the maximum production mode of operation, the flow of absorption medium into the absorption zone is set at a maximum allowable value and the rate of flow of feed entering the absorption zone in controlled in response to the rate of absorption medium flow, the feed stream analysis and flow rate, and the analysis of the overhead stream leaving the absorption zone. In the maximum efficiency mode of operation, the flow of feed material to the absorption zone is controlled in substantially the same manner and the flow of the absorption medium to the absorption zone is additionally controlled in response to the analysis and flow rate of the feed stream entering the absorption zone, and a desired nominal flow rate of feed material to the absorption zone. In one preferred embodiment of the invention the composition of the overhead stream leaving the absorption zone is also used to control the flow of absorption medium to the absorption zone.

Additional objects and advantages of the invention will be apparent from the following description of a preferred embodiment of the invention and explanation of the drawing in which.

Although the invention is illustrated and described in terms of a specific absorption process, the applicability of the use of the inventive method and apparatus described herein extends to other absorption processes and similar chemical processes. Lines designated as signal lines in the drawings can be electrical, pneumatic, mechanical, hydraulic, or other signal means for transmitting information. In almost all control systems, some combination of these types of signals will be utilized. Use of any other type of signal transmission compatible with the process and equipment in use, however, is within the scope of the invention.

The invention is particularly well suited for use with absorption processes wherein the rate at which the absorption medium can be supplied to the absorption zone is the factor which limits the effective capacity of the process.

Figure 1A:
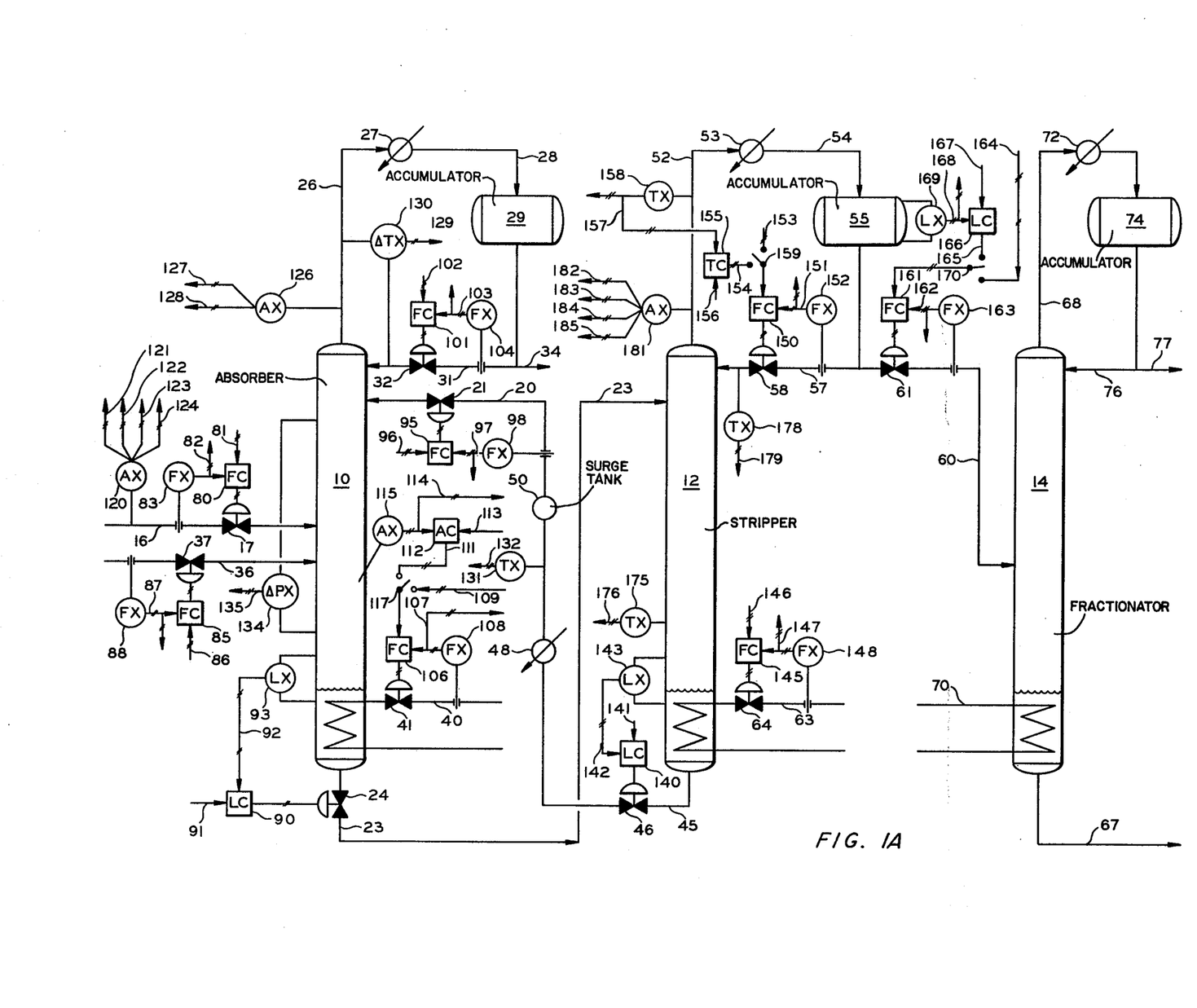
FIG. 1A is a schematic diagram of a process which can be controlled by means of the invention.

Referring now to the drawing and to FIG. 1A in particular, there is illustrated an absorption process having an absorption column 10 and a stripping column 12. An output of the absorption process is provided as the input to a fractionating column 14. A feed stream enters the absorption column 10 through a feed stream conduit 16, the flow of the feed to the absorption column 10 being controlled by a valve 17 located in the feed stream conduit 16. An absorption medium stream enters the absorption column 10 through an absorption medium conduit 20 and a control valve 21 located in the absorption medium conduit 20. Inside the absorption column 10 the feed material is contacted by the absorption medium. Those constituents of the feed material which are absorbed by the absorption medium accumulate with the absorption medium at the bottom of the absorption column 10 and are removed from the absorption column through the absorber bottom conduit 23 and control valve 24 associated therewith. Those constituents of the feed stream which are not absorbed by the absorption medium leave the absorption column through the absorber overhead stream conduit 26. A cooling heat exchanger 27 at least partially condenses the overhead product of the absorption column 10, and the resulting at least partially condensed overhead product is passed through a conduit 28 to an absorber overhead accumulator 29. A portion of the liquid contents of the absorber overhead accumulator 29 is returned to the absorption column 10 through an absorber reflux conduit 31 and its associated control valve 32. The remainder of the liquid contents removed from the absorption overhead accumulator 29 are removed from the process by an absorber product conduit 34. If desired, a recycle feed stream from a subsequent process or other similar source may also be introduced into the absorption column 10 through a recycle feed conduit 36 and its associated control valve 37. The absorption column 10 is equipped with a reboiler section located at the bottom of the column. A heating fluid can be supplied to the reboiler section of the absorption column 10 through an absorber reboiler steam conduit 40 and its associated control valve 41.

Conduit 23 carries the bottom product of the absorption column 10, containing the absorption medium and those constituents of the feed stream and recycle feed stream which have been absorbed, to the stripping column 12. In the stripping column 12 the constituents absorbed in the absorption medium are separated from the absorption medium. The absorption medium accumulates at the bottom of the stripping column 12 and is recycled through the stripper bottom conduit 45 and its associated control valve 46 to a cooling heat exchanger 48, a surge tank 50, and the absorption medium stream conduit 20 associated with the absorption column 10. The constituents which are separated from the absorption medium in the stripping column 12 are removed from the stripping column 12 through the stripper overhead conduit 52, a cooling heat exchanger 53, and a conduit 54 to the stripper overhead accumulator 55. A portion of the liquid material removed from the stripper overhead accumulator 55 is returned to the stripping column 12 through a stripper reflux conduit 57 and its associated control valve 58. The remainder of the liquid material removed from the stripper overhead accumulator 55 is carried through the stripper output conduit 60 and its associated control valve 61 to the fractionation column 14. A reboiling zone is located at the bottom of the stripping column 12. Thermal energy is supplied to the reboiling zone by circulating steam or other suitable fluid through conduit 63 and its associated control valve 64.

The fractionating column 14 accepts the material flowing to it through the stripper output conduit 60 as feed and divides the feed into a bottoms product leaving the fractionation column 14 through the fractionator bottom conduit 67 and an overhead vapor stream leaving the fractionation column 14 through the fractionator overhead conduit 68. Heat is supplied to a reboiler zone at the bottom of the fractionation column 14 through a steam conduit 70. The material leaving the fractionation column 14 through the fractionator overhead conduit 68 can be cooled by a cooling heat exchange unit 72 and passed to an accumulator 74. A portion of the material from the accumulator 74 can be returned to the fractionation column 14 through a fractionator reflux conduit 76 and the remainder of the material in the accumulator 74 is removed from the process through a fractionator overhead output conduit 77.

Although the invention is illustrated in conjunction with the apparatus of the absorption column 10, the stripping column 12, and the fractionation column 14 as hereinbefore described, the invention is equally applicable to similar systems utilizing different equipment arrangements. For example, each of the columns schematically illustrated can, in actuality, be a plurality of columns connected to perform the function of a single larger column. Likewise, the reboiling zones of the various columns can be external to the actual column structure rather than being incorporated into the bottom portion of each column as illustrated. Various additional conventional equipment such as pumps, valves, heat exchange by-pass conduits and other conventional equipment associated with the schematically illustrated process have not been specifically illustrated in FIG. 1A but are known by those skilled in the art to be a part of a process such as the one illustrated. With regard to the fractionation column 14, all controls and a substantial amount of conventional equipment have been omitted from the schematic illustration. All additional equipment and controls ordinarily associated with a conventional distillation column can be associated with the fractionation column 14.

Although the equipment schematically illustrated in FIG. 1A can be utilized for a number of purposes, further discussion of the invention will be in terms of a butadiene purification unit wherein the absorption column 10 is a furfural absorber, the stripping column 12 is a furfural stripper, and the fractionation column 14 is a butadiene purification column. Although it could be derived from other sources, the feed entering the absorption column 10 through feed stream conduit 16 can be the effluent from an oxidative dehydrogenation reaction unit which converts butylenes to butadiene. The feed may also contain varying amounts of raw butadiene from other sources. A representative composition of the feed entering the absorption column 10 through the feed stream conduit 16 would be about 5 percent butanes, about 15 percent butene-1, about 10 percent trans-2-butene, about 15 percent cis-2-butene, about 55 percent butadiene, and a trace amount of vinyl acetylene. Furfural entering the absorption column 10 through the absorption medium conduit 20 is utilized to selectively absorb the butadiene constituent of the feed material and to thereby separate the butadiene from the butenes. The primary purpose of the absorption column 10 is to make a separation between butene-1 and butadiene. The material removed from the absorber overhead accumulator 29 through the absorber by-product conduit 34 can be recycled to an oxidative dehydrogenation reaction unit or can be further processed to yield a butene-1 product. The bottom product of the absorption column 10 containing furfural with butadiene and portions of other feed constituents absorbed therein is passed through the absorber bottom conduit 23 as feed to the stripping column 12.

The purpose of the stripping column 12 is to make a separation between furfural and the hydrocarbons absorbed therein. The stripped furfural leaves the stripping column 12 through stripper bottom conduit 45, is cooled by the cooling heat exchanger 48, and is recycled through the surge tank 50 and the absorption medium conduit 20 to the absorption column 10. The material leaving the stripping column 12 through the stripper overhead conduit 52 is cooled and condensed by the cooling heat exchanger 53 and is delivered by conduit 54 to the stripper overhead accumulator 55. That portion of the material leaving the stripper overhead accumulator 55 which is not returned to the stripping column 12 as reflux is carried by the stripper output conduit 60 as feed to the fractionation column 14.

The fractionation column 14, a conventional distillation column, separates butadiene from less volatile hydrocarbons. The overhead product of the fractionation column 14 is removed through the fractionator overhead output conduit 77 as a commercial butadiene sales product. The heavier constituents of the feed entering the fractionation column 14 through the stripper output conduit 60 can be recycled to the oxidative dehydrogenation reaction unit through the fractionator bottoms conduit 67 or can be stored and utilized for other purposes.

In general, each of the streams entering or leaving each column is controlled in some way. The control valves associated with the streams entering and leaving the absorption column 10 and the stripping column 12 are shown in FIG. 1A. Although the streams entering and leaving the fractionation column 14 can be similarly controlled, the valves and associated equipment, as previously indicated, have been omitted for ease of illustration.

Control valve 17 associated with feed stream 16 controls the rate of feed material flow to the absorption column 10 in response to the comparison by a flow controller 80 of the difference between a feed flow set point signal 81 and the actual feed flow signal 82 delivered by a feed flow transducer 83.

Control valve 37 associated with recycle feed stream 36 controls the flow rate of recycled butadiene feed entering the absorption column 10 in response to a comparison by flow controller 85 of the desired butadiene recycle feed flow rate, as represented by set point signal 86, and the actual butadiene recycle flow rate, represented by flow rate signal 87 which is delivered by flow rate transducer 88 in response to a measurement of the actual flow rate of the recycle feed stream 36.

The flow rate of material leaving the bottom of the absorption column 10 through absorber bottom conduit 23 is controlled by control valve 24 in response to a comparison by level controller 90 of a set point signal 91, representative of the desired liquid level in the bottom reboiler portion of the absorption column 10, and the actual reboiler liquid level, represented by a liquid level signal 92 delivered by liquid level transducer 93.

The flow of furfural to the absorption column 10 is regulated by control valve 21 associated with absorption medium stream 20 in response to a comparison by flow controller 95 of the difference between a set point signal 96, representative of the desired flow rate of furfural into the absorption column, and a flow rate signal 97, representative of the actual flow rate of furfural into the absorption column 10 as provided by furfural flow rate transducer 98.

The flow rate of reflux from the absorber overhead accumulator 29 to the absorption column 10 through the absorber reflux conduit 31 is controlled by control valve 32 in response to a comparison by flow controller 101 of a set point 102, representative of the desired reflux flow rate, and a reflux flow rate signal 103, representative of the actual reflux flow rate and delivered by reflux flow rate transmitter 104.

The rate of flow of steam through the absorber reboiler steam conduit 40 to the reboiler section of the absorption column 10 is controlled by control valve 41 in response to the output of a flow controller 106. The flow controller 106 is adapted to compare the actual flow rate of steam to the reboiler, as represented by steam flow rate signal 107 delivered by flow rate transducer 108, with either a set point 109, representative of the desired flow rate of steam to the reboiler, or the output signal 111 of analysis controller 112. The output signal 111 from the analysis controller 112 is delivered in response to a comparison by the analysis controller 112 of a set point signal 113, representative of the desired concentration of one or more constituents at a specific location within the absorption column 10, and analysis signal 114, representative of the actual concentration of the one or more constituents in question as measured by analyzer 115 from a sample withdrawn from the absorption column 10 at the point in question. A switching means 117 which can be either manually or automatically controlled selects either signal 109 or signal 111 as the set point for the flow controller 106.

Other control equipment associated with the absorption column 10 includes an analyzer 120 adapted to withdraw a sample of the feed entering the absorption column 10 through conduit 16 and deliver output signals 121, 122, 123, 124, which respectively represent the concentration of butanes, butene-1, trans-2-butene, and cis-2-butene. Another analyzer 126 is adapted to analyze the material leaving the absorption column 10 through the absorber overhead stream conduit 26 and to deliver signal 127 and 128 which respectively represent the concentration of butadiene and trans-2-butene in the absorber overhead stream. A temperature differential transducer 130 measures the difference in temperature between the absorber overhead stream within the absorber overhead stream conduit 26 and the temperature of the absorber reflux stream within the absorber reflux conduit 31 and delivers a signal 129 representative thereof. A temperature transducer 131 measures the temperature of the furfural stream leaving the cooling heat exchanger 48 and delivers a temperature signal 132 representative thereof. Differential pressure transducer 134 measures the difference in pressure between two predetermined points within the absorption column 10 and delivers a signal 135 representative of that difference. Additional control apparatus such as, for example, a valve controlling the rate of flow material through absorber by-product conduit 34 in response to a comparison by a flow controller of a set point signal representative of the desired liquid level in the absorber overhead accumulator 29 and a liquid level signal representative of the actual liquid level in the absorber overhead accumulator 29 delivered by a liquid level transducer, can also be added to the control means shown in FIG. 1A.

The flow of bottom product from the stripping column 12 is regulated by control valve 46 associated with the stripper bottom conduit 45 in response to a comparison by a level controller 140 in response to a comparison of a set point signal 141, representative of the desired liquid level in the reboiler portion of the stripping column 12, and a liquid level signal 142 representative of, and delivered by liquid level transducer 143 in response to the actual level of liquid within the reboiler associated with the stripping column 12.

The flow of steam through the stripper reboiler steam conduit 63 to the reboiler section of the stripping column 12 is regulated by control valve 64 in response to a comparison by a flow controller 145 of a set point signal 146, representative of the desired flow rate of steam to the reboiler, and a steam flow rate signal 147, representative of the actual rate of flow of steam to the reboiler and delivered by flow rate transducer 148.

The flow rate of overhead material from the stripper overhead accumulator 55 being returned to the stripping column 12 as reflux through the stripper reflux conduit 57 is regulated by control valve 58 in response to flow controller 150. The flow controller 150 compares the actual flow rate of the reflux material through the stripper reflux conduit 57, as represented by flow rate signal 151 generated by a flow transmitter 152, with either a set point 153 representative of the desired reflux flow rate or the output signal 154 delivered by temperature controller 155. The temperature controller 155 generates its output signal 154 in response to a comparison between a set point signal 156, representative of the desired temperature of material leaving the stripping column 12 through stripper overhead conduit 52, and temperature signal 157, representative of the actual temperature of the material within the stripper overhead conduit 52 as measured by a temperature transducer 158. A switching means 159, which may be either automatically or manually operated, is provided for selecting between set point signal 153 and temperature controller output signal 154 for use as a set point to the flow controller 150.

The flow rate of material leaving the stripping column 12 as feed to the fractionation column 14 through the stripper output conduit 60 is regulated by control valve 61 in response to a flow controller 161. The flow controller 161 is adapted to compare a flow rate signal 162 representative of the actual flow rate of material through the stripper output conduit 60, as delivered by flow transducer 163, with either a set point 164 or the output 165 of a level controller 166. The output 165 of the level controller 166 is determined in response to comparison of a set point signal 167, representative of a desired liquid level within the stripper overhead accumulator 55, and liquid level signal 168, representative of, and delivered by liquid level transducer 169 in response to, the actual level of liquid within the stripper overhead accumulator 55. A switch means, 170, which may be either automatically or manually operated, is provided for selecting between set point signal 164 and level controller output signal 165 for use as the set point to the flow controller 161.

Other control apparatus associated with the stripping column 12 includes a temperature transducer 175 which produces a temperature signal 176 representative of the temperature at a specified location within the stripping column 12, a temperature transducer 178 which produces a temperature signal 179 representative of the temperature of the reflux stream entering the stripping column 12 through the stripper reflux conduit 57, and an analyzer 181 which produces output signals 182, 183, 184, 185, which respectively represent the concentrations of butene-1, trans-2-butene, cis-2-butene, and vinyl acetylene within the material leaving the stripping column 12 through the stripper overhead conduit 52.

The method and apparatus of the invention can be implemented in conjunction with a variety of additional control methods and equipment. There are some control methods which are particularly compatible with the hereinafter described specific embodiments of the invention. For example, with regard to the absorption column 10, the reboiler steam flow is manipulated to control the butene-1 concentration leaving the bottom of the absorption column 10 and the overhead of the stripping column 12 by utilizing the output signals of analyzer 181 and other process parameters including material balance information to provide a set point signal 109 to flow controller 106. The flow of material through the absorber reflux conduit 31 is manipulated to compensate for thermal disturbances from the furfural cooling and reflux condensing systems by generating set point signal 102 in response to signals 129, 132, and 97. The cooling effect of cooling heat exchange means 48 is controlled in response to signal 132.

With regard to the stripping column 12, the flow rate of material through stripper reflux conduit 57 is manipulated to control the temperature of material leaving the stripping column through the stripper overhead conduit 52 by generating set point 153 for use by flow controller 150 in response to signals 157, 179 and 151. The flow of steam through reboiler conduit 63 is manipulated to indirectly control the stripping column reflux flow by generating set point signal 146 in response to signal 151 in a "slow" control loop.

Other additional and/or alternative control means can be used in conjunction with the method and apparatus of the invention.

In the maximum production mode of operation the control valve 21 associated with the absorption medium conduit 20 is set at a maximum open position by supplying to the flow controller 95 a set point signal 96 representative of a maximum allowable flow rate. The control valve 17 associated with the feed stream conduit 16 is then adjusted by flow controller 80 in response to variations in the set point signal 81. In this mode of operation set point signal 81 is adjusted to provide for the optimum feed flow which can be satisfactorily acted upon by the absorption medium entering the absorption column 10. Selection of the flow rate of the absorption medium into the absorption column at a maximum value is particularly advantageous when the absorption medium is furfural or some other similar relatively heavy medium since the valves, conduits, and other equipment associated with the furfural handling equipment connecting the bottom of the stripping column 12 with the furfural feed location of the absorption column 10 are more likely to become fouled or constricted by heavy or polymerized constituents in the furfural than are the valves and conduits handling other streams associated with the absorption column 10, stripping column 12, or fractionation column 14. If the conduits and valves associated with the furfural handling system become constricted through continuing use, therefore, operation in the maximum production mode will continue to provide the maximum output of which the system is capable by utilizing all the available furfural flow.

In the maximum efficiency mode of operation both set point 81 and set point 96 are varied in order to optimize both the flow of feed and the flow of absorption medium necessary to most efficiently separate the feed constituents. In this mode the flow rates of the absorption medium and feed material to the absorption column 10 are regulated in response to actual process conditions and in response to each other.

Whenever the material being removed from the stripper overhead accumulator 55 through the stripper output conduit 60 is being provided directly as feed for an additional process or separation the control valve 61 associated with the stripper output conduit 60 is operated with the set point signal 164 being provided to the flow controller 161 through the switch 170. The set point 164 is altered to take into account predicted changes in the flow of material into the stripper overhead accumulator 55, and is further modified to provide for a nonlinear relationship between the amount by which the liquid level within the stripper overhead accumulator 55 differs from the desired liquid level and the amount of correction made to the set point signal 164 causes by that difference. In this way variations in the flow of material through the stripper output conduit 60 are minimized (see FIG. 4).

Figure 1B:
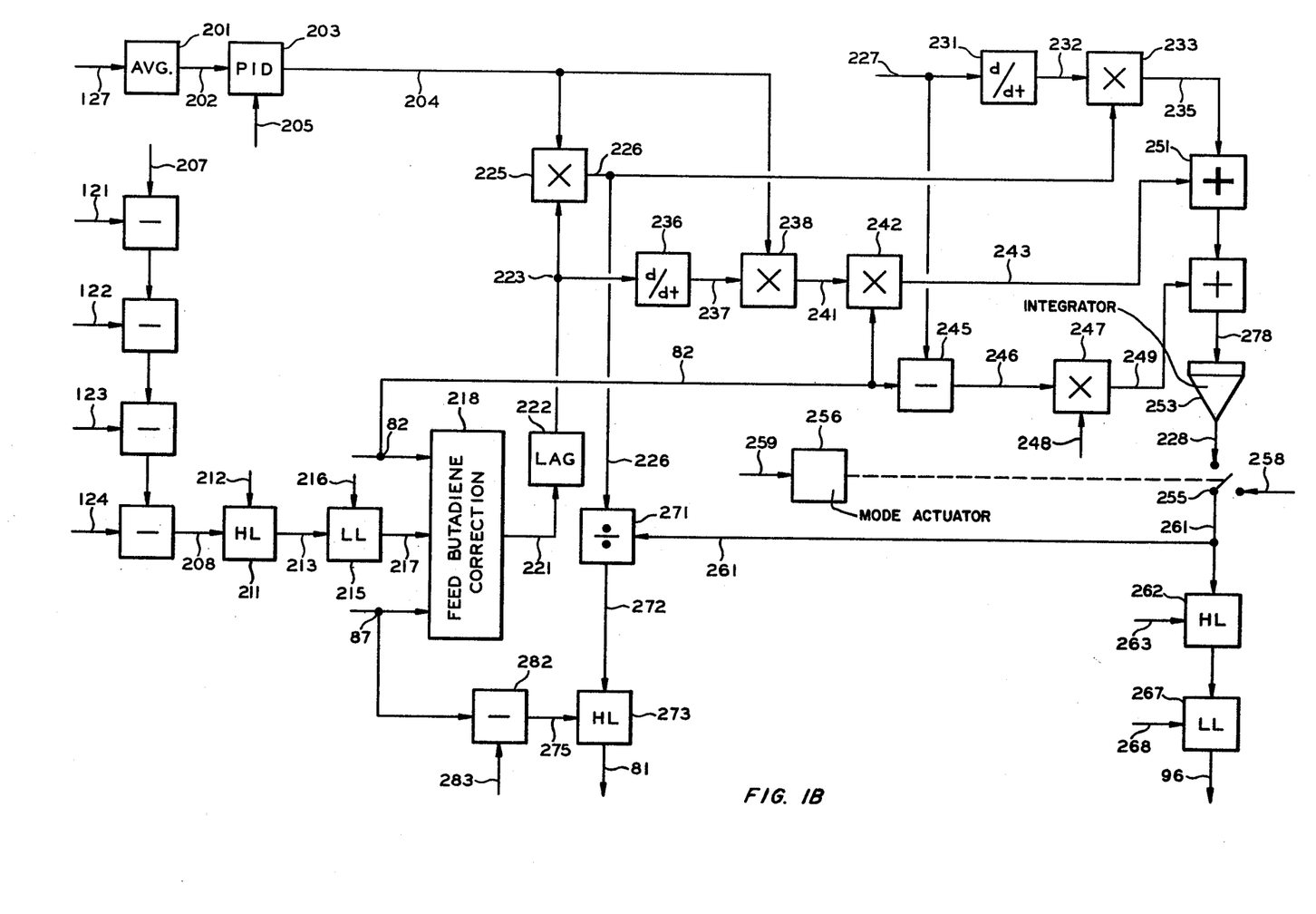
FIG. 1B is a schematic block diagram of the production of feed flow rate and absorption medium flow rate set points.

FIG. 1B illustrates a schematic representation of the generation of the feed flow set point 81 and the absorption medium flow set point 96. Referring to FIG. 1B in detail, signal 127 representative of the amount of butadiene in the overhead stream of the absorption column 10, as measured by analyzer 126, is averaged by an averaging means 201 to produce a signal 202 representative of the average concentration of butadiene in the overhead stream of the absorption column 10. Signal 205 is a set point signal representative of the desired maximum concentration of butadiene in the absorber overhead stream 26. Signal 202 is used as an input to a proportional-integral-derivative controller 203 which produces, from signal 202 and set point signal 205, a signal 204 representative of the desired ratio of furfural flow entering the absorption column 10 to butadiene flow entering the absorption column 10. Signal 127 can be used in place of signal 202 as the input to the proportional-integral-derivative controller 203, if desired. Averaging of the signal 127 to produce an average signal 202 is considered to be preferable, however, since temporary variations in the composition of the overhead product of the absorption column 10, variations in output caused by some transient condition within the analyzer 126, and other similar temporary disturbances will be minimized in producing signal 204. In general, a running average of sufficient duration to minimize the effects of inconsequential temporary variations in signal 127 and short enough to provide accurate control response to significant changing conditions within the process is desirable. Ordinarily averaging of at least two successive analyzer outputs is desirable, with averaging of at least three successive analyzer outputs being preferred. In terms of time, averaging of the analyzer output over an immediately preceding period of from about 10 minutes to about 60 minutes is desirable, and averaging over an immediately preceding period of from about 15 minutes to about 30 minutes is preferred.

The proportional-integral-derivative means 203 can be any of a number of such control mechanisms familiar to those skilled in the art. In general, such a means will act in response to a normalized error signal which is equal to the term $K_n(M-S)$ where $K_n$ is a normalization factor, M is the input measurement and S is the set point signal. The output of the proportional-integral-derivative (P-I-D) means will ordinarily be equal to the sum of a proportional term having a proportional gain constant $K_p$, an integral term having an integral time constant $T_i$ and an additional integral gain constant $K_i$, a derivative term having a derivative time constant $T_d$ and an additional derivative gain constant $K_d$, and can also have a lag term having a lag time constant $T_L$ and an additional lag gain constant KL. In any particular P-I-D means, one or more of the terms may be equal to zero and/or two or more of the terms may be combined or interrelated. Selection of the proper constants and parameters to be employed in the proportional-integral-derivative means 203 in order to yield the desired output signal 204 can be determined based on theoretical and/or experimental determinations of the operating characteristics of the absorption column 10. When experimental observations are utilized as a basis for designing and tuning the proportional-integral-derivative means, mathematical analysis, such as multiple regression analysis, of the experimental data can be used to aid in the determination of a suitable control system.

signals 121, 122, 123, and 124 respectively representative of the concentration of butanes, butene-1, trans-2-butene, and cis-2-butene in the feed material flowing through the feed stream conduit 16 to the absorption column 10 are subtracted from a set point signal 207 representative of a 100 percent concentration of butadiene in the feed material to yield a signal 208 representative of the concentration of butadiene in the sample analyzed by the analyzer 120. Although analysis of the feed stream to detect and directly measure the concentration of butadiene in the feed material is within the scope of the invention, measurement of all other significant constituents in the feed material is preferred when all constituents in the feed material are known and when the butadiene concentration is high. The analysis and measurement of all other feed constituents followed by subtraction to determine the concentration of butadiene in the feed is preferred since the greater accuracy with which the constituents of lower concentration can be measured, using chromatographic techniques, for example, permits a greater accuracy in the determination of butadiene concentration than would an attempt to measure the concentration of the major constituent directly.

A high limit control means 211 compares signal 208 with a set point signal 212 and delivers a signal 213 in response to the comparison. If the signal 208 is less than or equal to the set point signal 212, signal 213 will be equal to signal 208. If signal 208 is greater than set point signal 212, however, signal 213 will be equal to signal 212. A low limit means 215 compares signals 213 to a set point signal 216 and delivers a signal 217 in response to the comparison. If the signal 213 is greater than or equal to the set point signal 216, signal 217 will be equal to signal 213. If signal 213 is less than signal 216, signal 217 will be equal to signal 216. Together, the high limit means 211 and the low limit means 215 will produce a signal 217 which is equal to signal 208 unless signal 208 is greater than a set point signal 212 or less than a set point signal 216. If signal 208 is greater than set point signal 212, signal 217 will be equal to signal 212. If signal 208 is less than signal 216, signal 217 will be equal to signal 216. The operation of the high limit and low limit means on the signal 208 representative of the butadiene concentration in the feed material prevents use of signal 208 for control purposes if that signal is outside of a preselected range. In this way, an error in analyzer output, or some other similar eqipment malfunction, is not permitted to exert an undue influence over the control system.

A feed butadiene correction means 218 accepts signal 217, signal 82, representative of the rate of feed flow through conduit 16, and signal 87, representative of the recycle feed flow through recycle feed stream conduit 36, and generates a signal 221 representative of the total concentration of butadiene in all feed being carried to the absorption zone 10. If no recycle feed stream is passed to the absorption column 10 or if the recycle feed stream is so small as to be insignificant when compared to the main feed stream, correction means 218 is not necessary and signal 217 can be used as the input to lag means 222 in place of signal 221. Correction means 218 can utilize any of a number of available techniques to compare the flow rates of main and recycle feed and to produce an output representative of total feed butadiene concentration. If the concentration of butadiene in the recycle feed is not substantially constant, an additional input representative of that concentration should be provided to the correction means. Ordinarily, however, a recycle feed stream will maintain a substantially constant composition and this concentration can be incorporated into the correction means 218 as a constant. A first order or other suitable lag means 222 converts signal 221 to a signal 223, representative of the concentration of butadiene entering the absorption column 10, suitable for control purposes. Signal 223 takes into account the process dynamics of the absorption column 10 and its related equipment and control systems. The necessary time constant and other parameters, if any, of the lag means 222 can readily be determined by a person skilled in the art from theoretical calculations and/or analysis of experimental data.

A multiplier 225 accepts signals 204 and 223, representing the desired ratio of the flow rates of furfural to butadiene entering the absorption column 10 and the concentration of butadiene entering the absorption column respectively. From signals 204 and 223 multiplier 225 produces an output signal 226 representative of the desired ratio of furfural flow to feed flow entering the absorption column 10.

A signal 227 is representative of the nominal desired continuing flow of feed material to the absorption column 10. Signal 227 may be representative of the nominal rate at which feed material must be used to keep the absorption column 10 from becoming a plant bottleneck, for example. Signal 227 can also be a constant based on the average rate of production of an oxidative dehydrogenation reaction unit providing feed to the absorption column 10 or can be varied in response to varying requirements for processing of feed material by the absorption column 10. From signals 82, 223, 226, and 227 a signal 228 representative of the optimum furfural flow rate to the absorption zone 10 is determined. If signal 82, representative of an actual flow measurement, is noisy and adequate filtering is either impossible or impractical, set point signal 81 associated with flow rate signal 82 can be used in place of signal 82 in this determination. Signal 227 is differentiated with respect to time by differentiating means 231 to produce signal 232. Multiplying means 233 accepts signals 232 and 226 as inputs and produces an output signal 235 representative of the product of its two inputs. Differentiating means 236 determines the rate of change with respect to time of signal 223 and produces an output signal 237 representative thereof. Multiplying means 238 accepts signals 204 and 237 and produces an output signal 241 representative of the product of its two inputs. Multiplying means 242 accepts signals 82 and 241 as inputs and produces an output signal 243 representative of the product of its input signals. Subtracting means 245 accepts input signals 82 and 227 and delivers an output signal 246 representative of the difference between the actual flow rate of feed material through feed stream conduit 16, as represented by signal 82, and the desired average flow rate of feed material through feed stream conduit 16, as represented by signal 227. Multiplying means 247 multiplies signal 246 by a constant 248 and delivers an output signal 249 representative of the product of its multiplication. Adding means 251 and 252 combine to add signals 235, 243, and 249, to yield signal 278. Signal 278 is then integrated by integrating means 253 to generate signal 228 representative of the optimum furfural flow rate.

A mode selection means 255 with its associated actuating means 256 selects between signal 228 and a set point signal 258 representative of a maximum allowable flow rate of furfural into the absorption column 10. A mode control signal 259 has a first condition which causes the actuating means 256 and mode selection means 255 to select signal 258 as the selected furfural flow rate signal 261. When signal 259 is in a second condition signal 228 will become the selected furfural flow rate signal 261. When signal 259 is in its first position, therefore, the furfural flow rate and the rate of production of butadiene will be maximized. When the signal 259 is in its second condition the efficiency of butadiene production will be optimized. Signal 259 may be generated by automatic means so that the process will be operated in the maximum efficiency mode until conditions require a change to the maximum production mode. For example, a low product storage tank level signal indicating a depletion of product inventory could be used as signal 259 or could be used to place signal 259 in its first position. In the same manner a signal such as a tank high level signal indicating an excess of feed material in feed storage might also be used to place signal 259 in its first position. Provision can also be made for manually changing the condition of signal 259 in response to conditions such as consumer product demand, feed material supply, and other conditions not susceptible to automatic interrogation.

The selected furfural flow rate signal 261 is transmitted to high limit means 262 having a set point 263 and the output of high limit means 262 is transmitted to low limit means 267 having a set point 268. The effect of high limit means 262 and low limit means 267 on the selected signal 261 is to produce a furfural set point signal 96 which is the same as the selected furfural flow rate signal 261 when signal 261 is greater than or equal to signal 268 and less than or equal to signal 263. When signal 261 is greater than signal 263, signal 263 will be used as the set point signal 96. When signal 261 is less than signal 268, signal 268 will be used as the set point signal 96. In this way this furfural set point signal 96 is maintained within a preselected range and the distruption caused by an erroneous measurement or equipment failure in the generation of the selected furfural flow rate signal 261 is minimized.

Figure 2:
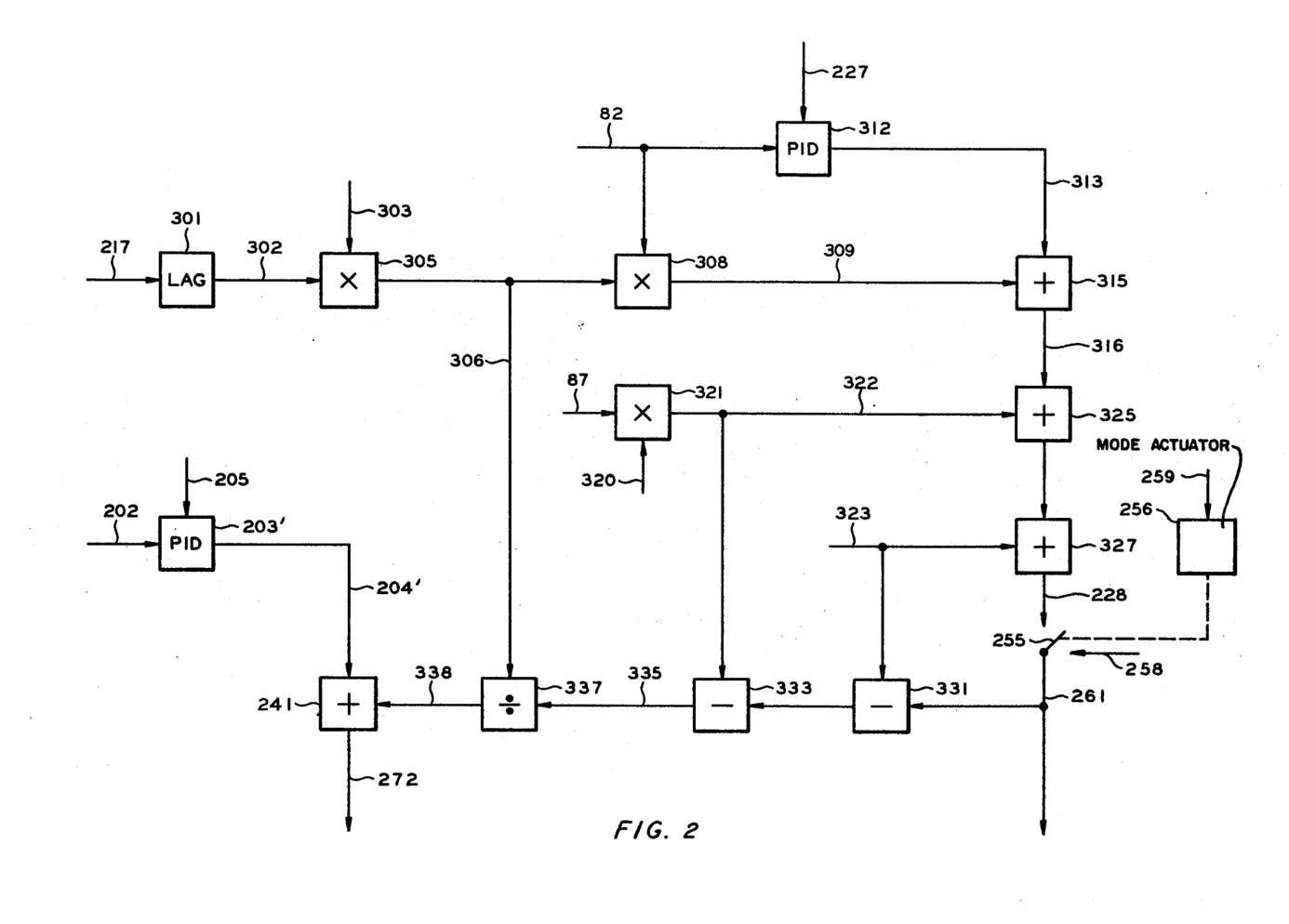
FIG. 2 is a schematic block diagram of an alternative embodiment of a portion of the FIG. 1B block diagram.

Dividing means 271 produces an output signal 272 in response to the division of signal 261, representative of the selected furfural flow rate, by signal 226, representative of the desired ratio of furfural flow rate to feed flow rate. Signal 272 is therefore representative of an optimum feed flow rate corresponding to the selected furfural flow rate. High limit means 273 compares signal 272 with set point signal 275 and delivers a feed set point signal 81 equal to signal 272 whenever signal 272 is less than or equal to signal 275. In the event that signal 272 is greater than signal 275, signal 275 will be utilized as the feed flow set point 81. In this manner high limit means 273 prevents an undesirably high flow of feed to the reaction zone. Set point signal 275 can be a fixed signal or can be generated in such a manner as to compensate for actual process conditions. As illustrated in FIG. 2, one method of generating signal 275 is to subtract the recycle flow rate signal 87 from a maximum total flow rate set point signal 283 utilizing subtracting means 282 in order to generate, as a result of the subtraction, signal 275. In this way it is possible to place an upper limit on the feed flow set point 81 controlling the flow of feed material to the absorption column 10 through feed stream conduit 16 in order to prevent the total flow of feed material to the absorption column 10 through feed stream conduit 16 and recycle feed stream comduit 36 from exceeding a desired maximum.

Utilizing the control apparatus of the method illustrated by FIG. 1B, the nominal or average desired continuing flow of feed material to the absorption column 10, as represented by signal 227, is used, along with process measurements, to generate an optimum furfural flow rate signal 228, taking into account process dynamics and similar conditions. In the maximum efficiency mode the optimun furfural flow rate signal 228 is utilized, along with other process measurements, to generate a corresponding optimum feed flow rate signal 272. In the maximum production mode of operation wherein the flow rate of furfural is maximized, the set point signal 258 representative of the maximum allowable flow rate of furfural into the absorption column 10 is utilized in place of signal 228 to generate the corresponding optimum feed flow rate signal 272. Although the specific method and apparatus illustrated by FIG. 2 are primarily suitable for use in conjuction with systems wherein the optimum ratio of furfural flow to feed flow over a wide range of production rate remains substantially constant, the invention is equally well adapted for control of similar processes in which the proportion of furfural flow to feed flow is subject to substantial variation as the production rate is increased or decreased. One implementation of the invention suitable for use with a process in which such variations can be expected is illustrated by FIG. 2.

Referring now to FIG. 2, the feed butadiene concentration signal 217, feed flow rate signal 82, recycle feed flow rate signal 87, and the nominal desired feed flow rate signal 227 are as previously defined in conjunction with the description of FIG. 1B. Signal 217 is acted upon by first order lag means 301 to produce a signal 302 representative of the lagged concentration of butadiene in the feed material entering the absorption column 10 through the feed stream 16. A multiplying means 305 produces an output signal 306 which is the product of signal 302 and a scaling factor signal 303. Signal 306 is therefore directly related to the concentration of butadiene in the feed stream. A multiplying means 308 produces an output signal 309 as a product of the multiplication of signals 306 and 82. Signal 309 is representative of a desired amount of furfural flow resulting form the composition and flow rate of feed material to the absorption column 10.

A proportional-integral-derivative (P-I-D) means 312 produces an output signal 313 representative of the amount of furfural required to be delivered to the absorption column 10 resulting from the difference between signal 82 representing the actual flow rate of feed material to the absorption column and signal 227 representing the nominal desired flow rate of feed material, and due to the dynamic characteristics of the process. An adding means 315 adds signals 313 and 309 to produce an output signal 316 representative of the amount of furfural required to be delivered to the absorption column 10 as a result of the feed composition, feed flow rate, and air between actual and desired feed flow, taking into account the dynamic features of the process. If no recycle feed stream is utilized in the process, or if the amount of material delivered to the absorption column10 by the recycle feed stream is sufficiently small, signal 316 can be used as a furfural flow set point.

When recycle feed flow is significant, a multiplying means 321 produces an output signal 322 as the product of the multiplication of signal 87 representing the flow rate of recycle feed material to the absorption column 10 and a scaling factor signal 320. Signal 322 is representative of the amount of furfural required to absorb the butadiene being carried to the absorption column 10 by the recycle feed conduit 36. Arriving at an amount of furfural required to handle the absorption of butadiene in the recycle feed can be accomplished in this manner since the recycle feed flow to the absorber in most absorption processes is of substantially uniform composition and is small in amount as compared to the flow rate of fresh feed to the absorption column. Under circumstances where a varying recycle feed composition and/or a varying recycle feed flow rate are large enough to substantially alter the dynamic response of the process, a signal containing information equivalent to that contained in signal 322 would necessarily be generated in a manner similar to the generation of signal 316.

A constant signal 323 is representative of an amount of furfural flow rate required for proper operation of the absorption column 10 in excess of the amounts of furfural required by the butadiene content and flow rates of butadiene-containing streams entering the absorption column 10. Expressed in other terms, signal 323 represents the amount by which the furfural flow should exceed the amount otherwise required to absorb the butadiene entering the absorption column in order to maintain a desirable operating condition within the absorption column 10. Adding means 325 and 327 sum signals 316, 322, and 323 to generate the optimum furfural flow set point signal 228. In a process where recycle feed flow is not present or is not significant, signals 316 and 323 can be added to produce a suitable set point signal 228. If signal 323 is small enough to ignore in any given process system, signal 316 or the sum of signals 316 and 322 can be used as a suitable set point signal 228, depending on whether or not recycle feed flow is significant.

The optimum furfural flow set point 228 is utilized in conjunction with a selection means 255 and maximum allowable set point signal 258 to generate a selected furfural flow set point 261 as previously described in conjunction with the explanation of FIG. 1B. Actuating means 256 and mode control signal 259 perform the same function and can be operated in the same manner as the correspondingly numbered elements of FIG. 1B.

In order to generate an optimum feed flow set point signal 272, signals 323 and 322 are first subtracted from the selected furfural set point signal 261 by subtracting means 331 and 333 to generate signal 335. Signal 335 is therefore representative of the selected furfural set point 261 less the amount, if any, of furfural flow required in excess of that necessary to absorb the butadiene entering the absorption column and less the amount, if any, of furfural flow required to absorb the butadiene contained in the recycle feed. In the maximum efficiency mode of operation wherein the optimum furfural set point signal 228 is utilized as the selected furfural set point signal 261, signal 335 will be identical to signal 316 and will be representative of the same furfural flow requirement. The dividing means 337 next divides signal 335 by signal 306 to generate a signal 338 representative of the amount of feed flow required as a result of the amount of furfural flow available to absorb the butadiene in the feed and the butadiene concentration in the feed material. An adding means 241 then adds signal 338 and a signal 204' to generate as a result of the addition the optimum feed flow set point signal 272. FIG. 204' is representative of the amount of feed flow required to maintain the concentration of butadiene in the overhead product of the absorption column 10 below the desired maximum. Signal 204' can be generated in substantially the same manner and using generally the same equipment as signal 204 of FIG. 1B. As illustrated by FIG. 2, signal 204' can be produced by a P-I-D means 203' utilizing the same measurement signal 202 and the same set point signal 205 as the P-I-D means 203 of FIG. 1B. P-I-D means 203 and P-I-D means 203' would have different tuning parameters but would otherwise be substantially the same.

Utilizing the implementation of the invention illustrated by FIG. 2 an absorption process can be controlled in the same dual mode manner, responsive to the same process measurements, and by means of the same generated set points as the embodiment illustrated by FIG. 1B.

Figure 1C:
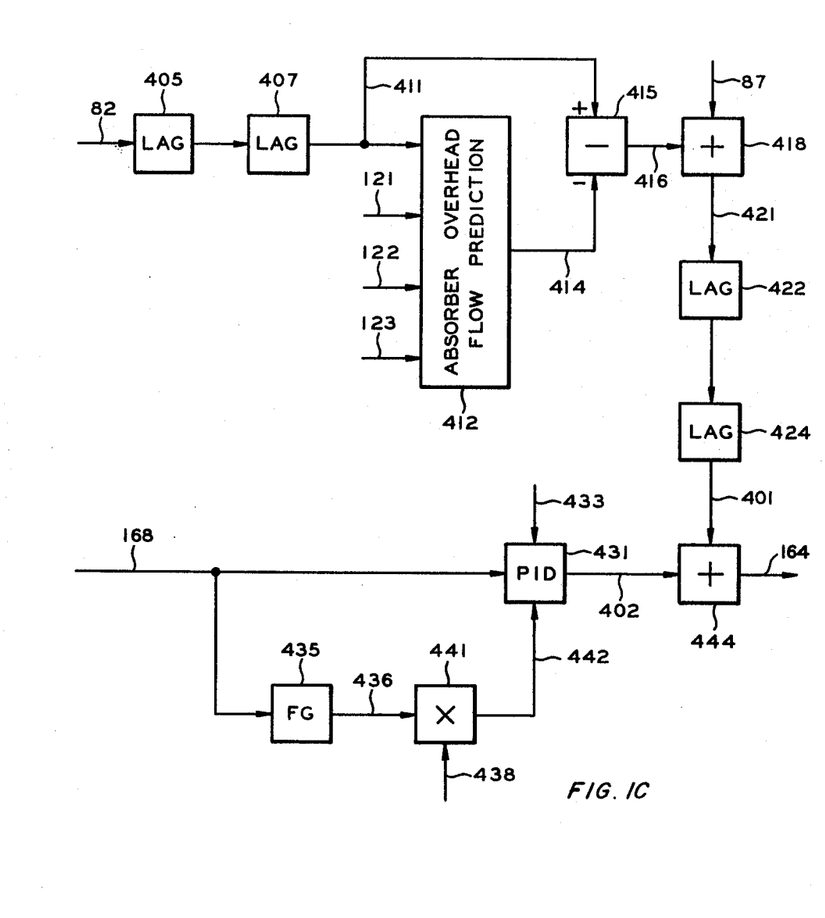
FIG. 1C is a schematic block diagram of the production of the output product flow set point.

FIG. 1C is a schematic representation of a method and apparatus by which set point signal 164, suitable for use as a set point to flow controller 161 associated with control valve 61 and the stripper output conduit 60, can be generated in response to signal 82, 87, 121, 122, 123, and 168. The set point signal 164 is generated by adding a signal 401 representative of the stripper output flow necessary to remove the predicted amount of material entering the stripper overhead accumulator 55 from the process and a signal 402 representative of the amount of flow through the stripper output conduit 60 necessary to maintain, or return to, a desired liquid level within the stripper overhead accumulator 55.

Signal 82, representative of the rate of flow of feed material to the absorption column 10 through the feed material conduit 16, as previously discussed in conjunction with the description of FIGS. 1B and 2, is acted upon by a first order lag means 405 and a first order lag means 407 to produce a signal 411 representative of the total amount of feed material which can be expected to be leaving the absorption column 10 as a result of feed flow to the absorption column 10 at a rate represented by signal 82. A second order lag means could be used in place of the two successive first order lag means or other lag means known in the art could be utilized to generate signal 411 from signal 82, taking into account the applicable process dynamics. An absorber overhead flow prediction means 412 accepts signals 411, 121, 122, and 123 as inputs and generates in response thereto an output signal 414 representative of the predicted absorption column 10 overhead rate of material entering the absorption column 10 as feed through the feed stream conduit 16. Signals 121, 122, and 123 respectively represent the concentrations of butanes, butene-1, and trans-2-butene contained in the feed entering the absorption column 10 through the feed stream conduit 16 and are generated by an analyzer 120 (FIG. 1A). In any application where the concentration of various constituents in the feed stream is subject to significant change over a period of time which is not substantially in excess of the response time of the process control system, lag factors similar to those applied to signal 82 by lag means 405 and 407 would necessarily be applied to signals 121, 122 and 123. However, when the composition of the feed stream is not subject to rapid and/or significant variations, the actual constituent concentrations and the lagged feed flow signal are suitable for use in predicting an absorber overhead flow signal 144. Any of several available techniques can be used to generate signal 414. The most straightforward technique is to multiply the feed flow signal 82 by a factor, determined from signals 121, 122 and 123, representative of the percent of feed flow expected to be carried overhead from the absorber.

In order to determine the amount of feed material leaving the bottom of the absorption column 10, signal 414, representative of the feed material expected to leave the absorption column 10 through the overhead stream, is subtracted from signal 411 representative of the total amount of feed material leaving the absorption column 10, by subtraction means 415 to produce signal 416. In process applications not having a recycle feed stream, signal 416 will be representative of the total absorbed material leaving the bottom of the absorption column 10 with the absorption medium. when a recycle feed stream is part of the process, however, a more accurate determination can be made by taking into account the additional recycled material which will be leaving the bottom of the absorption column 10. If the recycle feed stream entering the absorption column 10 through the recycle feed stream conduit 36 contains a significant amount of material which can be expected to leave the absorption column 10 through the absorber overhead conduit 26 or if the recycle feed stream varies significantly in composition and/or flow rate rapidly enough to preclude assumption of a standard and constant recycle feed stream for control purposes, lag means and/or overhead flow predictive means such as those applied to the feed material flow rate signal 82 may be necessary in conjunction with the recycle flow rate signal 87. Because the recycle flow rate is usually small compared with the main feed stream flow, and because the recycle feed composition flow rate ordinarily does not change significantly in most processes, addition of the recycle feed stream flow rate signal 87 to signal 416 by adding means 418 can be utilized in most processes to generate a signal 421 representative of the total amount of absorbed material leaving the bottom of the absorption column 10. Where a recycle feed stream is not used or where the recycle feed stream is enough smaller than the main feed stream as to be insignificant, signal 416 could be used in place of signal 421.

Since substantially all of the absorbed material leaving the bottom of the absorption column 10 will be stripped from the absorption medium in the stripping column 12, signal 421 can be acted upon by first order lag means 422 and 424 to produce signal 401 representative of the flow of material into the stripper overhead accumulator 55. Other equivalent lag means can be used in place of the two first order lag means 422 and 424 in order to account for process dynamics associated with absorbed material being delivered to the stripping column 12, being separated from the absorption medium within the stripping column 12, and being carried overhead from the stripping column 12 through the cooling heat exchanger 53 to the stripper overhead accumulator 55.

Figure 3:
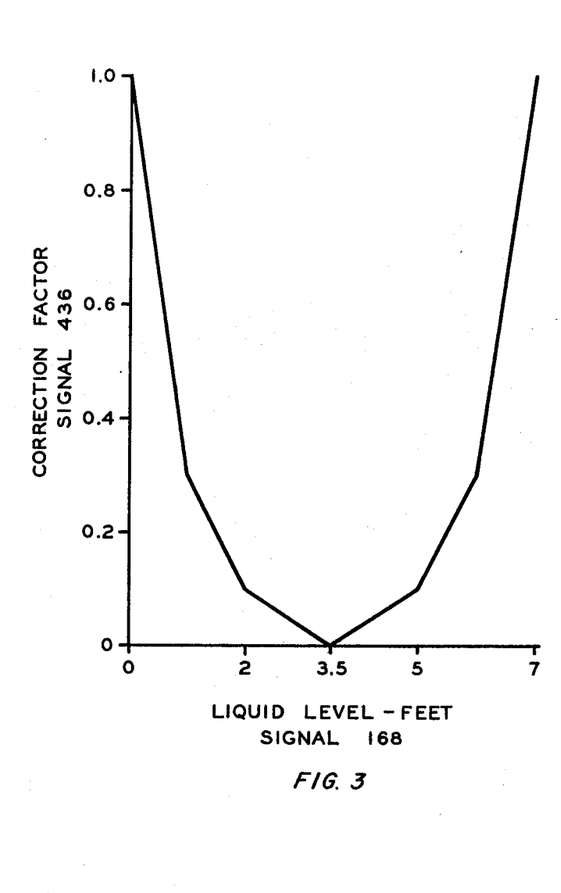
FIG. 3 is a graphical illustration of a suitable transfer function for use with the function generator of FIG. 4.

Signal 168, representative of the liquid level within the stripper overhead accumulator 55, is provided as an input to a P-I-D means 431 along with a set point 433 representative of the desired liquid level within the stripper overhead accumulator 55. In order to exert an additional degree of control in response to the stripper overhead accumulator liquid levels, signal 168 is also provided to a function generating means 435 which generates a correction factor signal 436 having a fixed relationship to signal 168. The relationship between signals 168 and 436 is preferably nonlinear in nature. An example of a preferred relationship between the output correction factor signal 436 and the input signal 168 of the function generating means 435 is illustrated by the graph of FIG. 3. Such a function can be generated using known pneumatic, hydraulic, electrical analog, electrical digital, or other similar techniques and apparatus. A multiplying means 441 produces an output signal 442 representative of the product of correction factor signal 436 and a constant tuning parameter signal 438. Signal 442 is then used as an input to the P-I-D means 431 in order to alter the ordinarily fixed parameters of the P-I-D means. Signal 402 will therefore vary in response to a change of liquid level within the stripper overhead accumulator 55 and in response to the difference between the level signal 168 and the set point signal 433, and will also vary as a result of the alteration of the tuning and response characteristics of P-I-D means 431 by signal 422 in response to changes in the liquid level signal 168. For a P-I-D means 431 of the type having a proportional term with a proportional gain constant $K_p$, an integral term having an integral time constant $T_i$ and an additional integral constant $K_i$, a derivative term having a derivative time constant $T_d$ and an additional derivative constant $K_d$, and a lag term having a lag time constant $T_L$ and an additional lag constant $K_L$, all responsive to a normalized error signal equal to $K_n(M-S)$ where $K_n$ is a normalization constant, M is the input measurement, and S is the set point, signal 442 can be used as signal $K_n$. For specific applications in which it is desirable, $K_i$, $K_d$ and/or $K_L$ can also be modified to achieve the desired response.

An adding means 444 adds signal 401, representative of the stripper product flow rate necessary to compensate for the amount of material being added to the stripper overhead accumulator 55, and signal 402, representative of the stripper product flow rate necessary to maintain the stripper overhead accumulator 55 liquid level at a desired value, to generate the stripper product flow rate set point signal 164 used by flow controller 161 to regulate the flow of material through control valve 61. Since the accumulator level can be higher or lower than desired, signal 402 can be either positive or negative and will therefore either increase or decrease the flow rate designated by signal 401 in producing signal 164.

FIG. 3 illustrates, in graphical form, a preferred response characteristic of a function generating means 435 suitable for use with a horizontally oriented, generally cylindrical stripper overhead accumulator 55 having a depth of approximately 7 feet with the desired liquid level being 3.5 feet. Use of a function generating means 435 having the characteristics exhibited by the graph of FIG. 3 permits the use of the nominal value of $K_n$ for the P-I-D means 431 to be used as signal 438. At very high or very low liquid levels signal 436 is near a value of 1.0 and the P-I-D means 431 is permitted to exercise its usual amount of control in the generation of signal 402. As the liquid level 168 approaches 3.5 feet, however, the multiplication of signal 438 by signal 436 decreases signal 442 and consequently decreases the amount of control which the P-I-D means 431 exerts in the generation of signal 402.

Although the function generator characteristics illustrated by FIG. 3 show a minimum correction factor of zero at the desired accumulator liquid level and provide a symmetrically increasing correction factor as the liquid level is increased or decreased from the desired level, placements of the minimum correction factor at a point other than the desired liquid level and/or use of a value other than zero as a minimum and/or use of a nonsymmetrical function are advantageous in making correction for the shape of an accumulator reservoir, for implementing a preference for variation from the desired level in one direction over variation in the opposite direction, or for other similar purposes.

Figure 4:
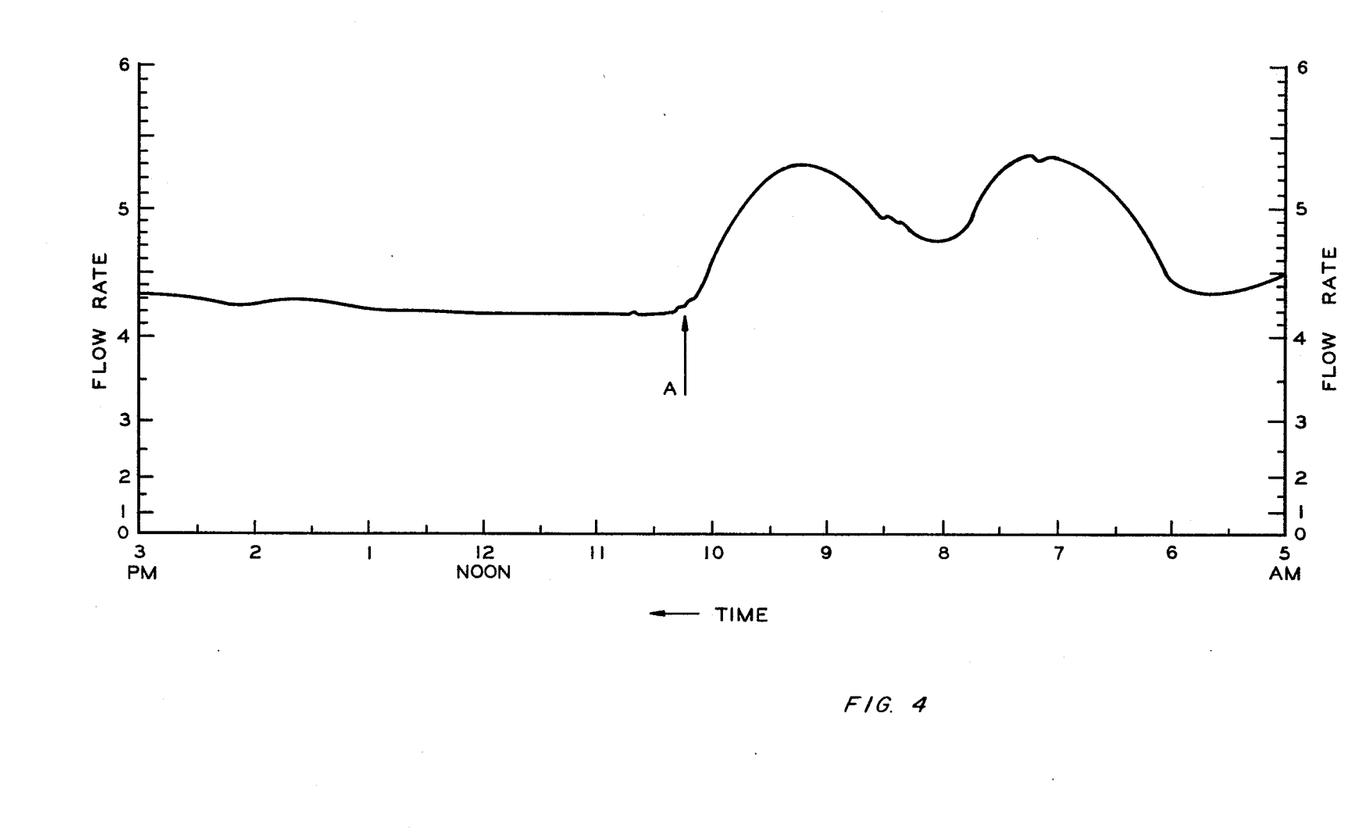
FIG. 4 is reproduction of operating data illustrating an advantage of the invention.

Implementation of the method and apparatus of the invention in the production of a set point signal 164 to control the product flow from a stripper overhead accumulator in a butadiene absorption, stripping, and purification process has resulted in a substantial improvement in the consistency of the flow rate of material to the fractionation column. FIG. 4 is a graphical representation of the flow rate of the stripper product stream beginning approximately 5 hours before and continuing until approximately 5 hours after the change from a conventional control system, which can be represented generally in terms of selection of signal 165 by switch 170 of FIG. 1A, to a control system utilizing signal 164, as shown in FIG. 1C, as the set point to flow controller 161. Due to the characteristics of the strip chart recorder and the original strip chart recording from which the curve of FIG. 4 has been transferred, the horizontal time scale reads from right to left and the vertical flow rate scale is nonlinear, with the vertical distance from the zero base line being equal to the square of the recorded flow. The time at which control in accordance with the invention was implemented is designated as point A. As FIG. 4 clearly illustrates, significant fluctuations in the flow of product from the stripping column were removed using the method and apparatus of the invention, permitting a substantial improvement in the uniformity of stripper output and fractionation column feed flow.

The apparatus illustrated in FIGS. 1B, 2, and 1C can be any known means for performing the indicated functions including electrical, mechanical, hydraulic, pneumatic, or other similarly operated apparatus adapted to automatically accept the indicated input signals and generate the indicated output signals responsive thereto. The apparatus of FIGS. 1B, 2 and 1C can be a programmed digital computer capable of utilizing various subroutines to implement the lag, P-I-D, function generating, and other necessary corrections. Those skilled in the art are capable of implementing the method of the invention utilizing any of the various pneumatic, hydraulic, mechanical, electrical analog and digital electrode techniques available to them as well as combinations of these various techniques.

These and other reasonable variations and modifications are possible within the scope of the foregoing disclosure and the appended claims to the invention.

I claim:

1. A method comprising:
   introducing an at least partially liquid input stream into a liquid accumulation zone;
   withdrawing a liquid output stream from said accumulation zone;
   establishing a liquid level signal representative of the liquid level within said liquid accumulation zone;
   generating from said liquid level signal a correction factor signal;
   utilizing said correction factor signal to modify the response of a proportional-integral-derivative means;
   providing said liquid level signal and a liquid level set point signal as inputs to said proportional-integral-derivative means to produce a first signal as the output of said proportional-integral-derivative means;
   establishing a second signal representative of the predicted flow rate of the liquid portion of said input stream into said accumulation zone, the flow rate of said input stream being independent of the liquid level in said accumulation zone;
   adding said first signal and said second signal to produce a third signal representative of the optimum flow rate of said output stream; and
   controlling the flow rate of said output stream in response to said third signal.

2. A method in accordance with claim 1 wherein the relationship between said liquid level signal and said correction factor signal is nonlinear.

3. A method in accordance with claim 1 wherein utilizing said correction factor to modify the response of said proportional-integral-derivative means comprises multiplying the modified response by said correction factor.

4. A method in accordance with claim 3 wherein said correction factor signal is zero when said liquid level signal is representative of the desired liquid level within said liquid accumulator.

5. Apparatus comprising:
   an accumulator vessel;
   an input conduit means operably connected with said accumulator vessel;
   an output conduit means operably connected with said accumulator vessel for withdrawing liquid therefrom;
   valve means for controlling the flow rate of liquid through said output conduit means;
   liquid level transducing means for measuring the level of liquid within said accumulator vessel and delivering a liquid level signal representative thereof;
   function generating means for generating, in response to said liquid level signal, a correction factor signal;
   proportional-integral-derivative means for generating a first output signal in response to said liquid level signal and a liquid level set point signal representative of a desired liquid within said accumulator vessel;
   means for altering at least one response characteristic of said proportional-integral-derivative means in response to said correction factor signal; and
   means for generating a second output signal representative of the predicted flow rate of liquid into said accumulator vessel through said input conduit means, the flow rate of said liquid into said accumulator vessel being independent of the liquid level in said accumulator vessel;
   means for adding said first output signal and said second output signal to produce an output set point signal; and
   means for controlling the operation of said valve means in response to said output set point signal.

6. Apparatus in accordance with claim 5 wherein said function generating means comprises means for producing a correction factor signal bearing a nonlinear relationship to said liquid level signal.

* * * * *